United States Patent
Snodderly et al.

(10) Patent No.: US 6,315,412 B1
(45) Date of Patent: Nov. 13, 2001

(54) METHOD AND APPARATUS FOR MEASURING VISUAL SENSITIVITY AND OPTICAL PROPERTIES OF COMPONENTS OF THE EYE

(75) Inventors: D. Max Snodderly, Lexington; Richard I. Land, Belmont; Billy R. Wooten, Rehoboth, all of MA (US)

(73) Assignee: The Schepens Eye Research Institute, Inc., Boston, MA (US)

( * ) Notice: Subject to any disclaimer, the term of this patent is extended or adjusted under 35 U.S.C. 154(b) by 0 days.

(21) Appl. No.: 09/555,736
(22) PCT Filed: Dec. 4, 1998
(86) PCT No.: PCT/US98/25770
  § 371 Date: Jun. 12, 2000
  § 102(e) Date: Jun. 12, 2000
(87) PCT Pub. No.: WO99/29229
  PCT Pub. Date: Jun. 17, 1999

Related U.S. Application Data
(60) Provisional application No. 60/067,852, filed on Dec. 5, 1997.

(51) Int. Cl.$^7$ .................................................. A61B 3/00
(52) U.S. Cl. ........................................ 351/200; 351/208
(58) Field of Search ...................... 351/200, 210, 351/211, 201, 202, 203, 238, 208, 209, 221; 600/544, 545

(56) References Cited

U.S. PATENT DOCUMENTS

| | | | |
|---|---|---|---|
| 4,861,154 | * 8/1989 | Sherwin et al. | 351/205 |
| 4,889,422 | * 12/1989 | Pavlidis | 351/210 |
| 5,331,969 | * 7/1994 | Silberstein | 600/558 |

OTHER PUBLICATIONS

Limits of Vision, Vision and Visual Dysfunction, vol. 5,, Dept. of Optometry & Vision Sciences, UMIST, Manchester, UK, 1991, Flicker as a Function of Wavelength and Heterochromatic Flicker Photometry, Peter K. Kaiser, pp. 171–190.

* cited by examiner

*Primary Examiner*—George Manuel
(74) *Attorney, Agent, or Firm*—Weingarten, Schurgin, Gagnebin & Hayes LLP

(57) ABSTRACT

A Non-Maxwellian, free viewing system capable of psychophysical measurement of visual sensitivity for the determination of ocular components is disclosed. The apparatus features electronically controlled light emitting elements whose outputs are variable with respect to intensity and temporal pattern, and can be combined by a small number of optical components. The light emitting elements can have outputs of different wavelengths, can be positioned at different retinal locations, and can be viewed through masks or apertures having different geometries. These features permit miniaturization of the device, and eliminate a major or experimental difficulty of light path alignment associated with larger systems, thus simplifying the measurement of macular pigment density compared to procedures used with a full sized optical bench.

16 Claims, 6 Drawing Sheets

METHOD AND APPARATUS FOR MEASURING VISUAL SENSITIVITY AND OPTICAL PROPERTIES OF COMPONENTS OF THE EYE

RELATED APPLICATIONS

This application claims priority from U.S. Provisional Application No. 60/067,852, filed Dec. 5, 1997, the whole of which is hereby incorporated by reference herein.

STATEMENT REGARDING FEDERALLY SPONSORED RESEARCH OR DEVELOPMENT

Part of the work leading to this invention was carried out with support provided by National Eye Institute Grant No. EY04911. Therefore, the U.S. Government has certain rights in the invention.

BACKGROUND OF THE INVENTION

Visual sensitivity is measured by determining how much light or how much change is needed for a subject to detect a stimulus. The necessary amount of light or change is affected by many factors, including the size, color, and temporal mode of presentation of the stimulus. In addition, sensitivity is a function of the location of the stimulus on the retina, and state of adaptation of the subject. Visual sensitivity declines with age and as a result of disease processes. Therefore, in order to determine the effectiveness of various efforts to reduce this decline, methods of measuring different types of visual sensitivity, including both light and dark-adapted sensitivity, as well as the rates of change of adaptation states, have been developed. Visual sensitivity measurements are also useful in determining the state of health of the retina and the neural pathways of the visual system. A further important use of the measurements of visual sensitivity is to determine the optical density of components of the eye.

One ocular component of importance is the yellow macular pigment, which is an accumulation of the carotenoids lutein and zeaxanthin in the foveal region of the retina. The spectral properties of this yellow pigment afford protection to the eye from short wavelength blue light. In addition, these two carotenoids are associated with retention of better visual sensitivity by older subjects. Therefore, assessing the in vivo concentration of macular pigment can be a valuable means of determining visual health. Lower macular pigment levels may also be associated with a higher risk of contracting age-related macular degeneration. Determination of in vivo macular pigment levels is possible, however, only if the amount of yellow pigment can be measured in situ.

The ability to measure the macular pigment concentration in situ results from the spectral characteristics of the yellow pigment itself: blue light, at a wavelength of 460 nm, is strongly absorbed by the yellow pigment whereas green light, at a wavelength of 560 nm, is not absorbed. The subject's own retina is used to perform both a baseline measurement and a foveal sensitivity measurement to obtain quantitative data about the amount of macular pigment in the fovea of the eye. Physical, in vivo, determinations of yellow macular pigment have been made using elaborate optical systems with many components [59]. Alternatively, the desired measurements can be obtained by psychophysical determinations.

Psychophysics is a hybrid field of science encompassing study of the perceptual (psychological) responses of subjects to sensory stimuli that are carefully controlled and measured by the methods of physics. For the visual system, light is the sensory stimulus. When light is absorbed by the photoreceptors of the retina, a neural response is generated that results in detection of the stimulus by the subject. The ocular tissues can be considered a set of optical filters through which the light must pass. By careful choice of the wavelength and the mode of presentation of the stimulus, the subject's responses can reveal the optical properties of the ocular filters. In essence, the visual system of the subjects is used as an intricate photosensory apparatus to measure the optical density spectrum of components of human ocular tissues.

The advantage of psychophysical methodology is that it is noninvasive, yet extremely sensitive. An individual can be followed over time, and the same tissue can be repeatedly measured. Psychophysical methods are therefore well suited to studying the effects of nutritional and environmental influences on the aging process. Nevertheless, psychophysical methodology has distinct limitations. The measurements usually require relatively prolonged testing by a skilled examiner. They can not be used with very young children, infirm or gravely handicapped individuals, or persons with dense cataracts that severely obscure vision. Furthermore, the subject must clearly understand the task and must be able to give reliable reports of sensory experience. This reliance on the participation and performance of the subject always introduces a risk of misunderstanding, with the need for careful cross-checking by the experimenter.

In the past, psychophysical methods have been used primarily in laboratories that have specialized and complex optical systems. Psychophysical determinations are most commonly made with a multi-channel Maxwellian-view optical bench set-up that requires operation by scientists with extensive experience with complex optical systems (e.g., [1, 8]). In Maxwellian view, the stimulus is imaged on the retina by an external lens that has a focal point centered in the subject's pupil. The beam of light that enters the eye is very small so that it only traverses the center of the subject's lens and does not intersect the subject's pupil. Aligning the subject's eye with the external Maxwellian lens, however, requires that the position of the head be precisely controlled. It is customary to make a "bite bar" with an impression of the subject's teeth so that when the subject rests the upper jaw on the bite bar, the head can be positioned to align the eye with the optical system. Once this is done, stimuli can be presented with the techniques of classical optics and the absorption of light by the macular pigment determined. One method of measuring this absorption uses flicker photometry. In this technique, two test colors are turned on and off at about 12 Hz (12 times per second). As the intensity of one of the test colors changes so that the test colors approach the same brightness, the perception of flicker diminishes. In using this method to measure macular pigment, the subject adjusts a blue light, alternating with a green light, until minimum or zero flicker is perceived. This setting, compared to a baseline, is a measure of visual sensitivity to blue light and, thus, the in vivo concentration of the blue-absorbing macular pigment.

A second major ocular component whose optical properties can be determined by visual sensitivity measurements is the lens of the eye. For these measurements, the dark-adapted visual sensitivity dominated by the rod photoreceptors can also be determined psychophysically. If the ocular media were perfectly transparent, the visual sensitivity of the observer would be determined solely by the visual pigment of the rod photoreceptors, rhodopsin [34]. Therefore, the deviation of the observer's sensitivity from the rhodopsin absorption spectrum provides a measure of the density of the ocular media, and most of this density is known to be due to the lens [35, 36]. Because the density spectrum of the lens is well known [36], the whole spectral curve can be estimated by measuring visual sensitivity at two or more wavelengths, which can be the same ones used to determine macular pigment.

Many disease states, as well as losses of function due to aging, appear to be preferentially evidenced by changes in the sensitivity of the pathway receiving inputs from the cone photoreceptors that absorb short-wavelength light, called the S-cone pathway. By alternating between two wavelengths that excite the S-cones but not the other cone types, it is possible to preferentially excite the S-cone pathway and measure its sensitivity. Attempts to improve S-cone pathway sensitivity by nutritional or other means can then be monitored to determine their effects and optimize the outcome of the interventions.

Thus, psychophysical determinations of ocular components can be useful for the assessment of a wide array of health-related conditions. The availability of an apparatus that was simpler to use for these determinations than the currently available complex systems would be desirable.

BRIEF SUMMARY OF THE INVENTION

A non-Maxwellian, free-viewing system capable of psychophysical measurement of visual sensitivity for the above purposes has been developed. The apparatus of the invention features electronically controlled light-emitting elements whose outputs are variable with respect to intensity and temporal pattern, and can be combined by a small number of optical components. The light emitting elements can have outputs of different wavelengths, can be positioned at different retinal locations and can be viewed through masks or apertures having different geometries.

These innovations permit miniaturization of the device and eliminate a major experimental difficulty of light path alignment associated with larger systems, thus simplifying the measurement of macular pigment density compared to procedures used with a full-sized optical bench. Also, the cost of the apparatus of the invention will be much less, in price and in construction time, than that of a conventional optical bench or an ophthalmic imaging system.

The small apparatus of the invention is simple to operate and to maintain and thus decreases the expense of making psychophysical measurements of visual sensitivity and the optical density of components of the eye. Therefore, use of this apparatus provides a readily accessible means for measuring visual parameters in relationship to dietary intake, effects of environmental exposure, and changes with age, as well as other personal characteristics of the subject.

Use of the information obtained from practicing the method of the invention can enable, e.g., nutritional counseling, lifestyle changes, or medical interventions for individual subjects whose density of macular pigment is too low for adequate protection. For individuals whose lens density is high compared to other people in their age group, the outcome of similar interventions to prevent development of cataract can be monitored. The simplicity and expected low cost of the device will make it feasible for it to be located in convenient geographical proximity to subjects who need to be examined frequently.

Because the apparatus is so small and light, it can easily be moved to different parts of the visual field. With the addition of appropriate positioning holders, it can therefore be used to test sensitivity of different regions of the retina. Measurements that can be performed with this device include sensitivity to: 1) different flicker rates, 2) different wavelengths, 3) flashes of different durations and repetition frequencies, and 4) temporal exchanges between stimuli of different wavelengths, including isoluminant flicker and stimuli designed to stimulate only one type of cone photoreceptor at a time. These tests are relevant to detection of many disease states, including age-related macular degeneration, glaucoma, and diabetic retinopathy, among others, as well as to the determination of loss of function due to aging.

BRIEF DESCRIPTION OF THE DRAWINGS

Other features and advantages of the invention will be apparent from the following description of the preferred embodiments thereof and from the claims, taken in conjunction with the accompanying drawings, in which:

DETAILED DESCRIPTION OF THE INVENTION

A traditional psychophysical method of presenting a target to the eye uses a Maxwellian view optical system. The Maxwellian view is produced when a lens forms a real image of a small source at the pupil of the eye. In the practice of the traditional method, the subject's head must be immobilized so that the image of the source does not fall outside the pupil and interrupt the light entering the eye. This immobilization requires use of a dental impression, which is time-consuming to make and cumbersome for a subject to keep in his or her mouth during the testing procedure. To control the wavelength, intensity, temporal pattern, and size of the stimulus, many optical and mechanical components must be interposed between the source and the final lens. Typical examples of a Maxwellian view optical system can be found in various references, e.g., [1, 11, 12].

An alternative prior art method is to project the stimulus onto a hemisphere so that the stimulus can be moved to different parts of the visual field. The subject's eye then images the stimulus on the retina. This method, often called perimetry [78], requires a relatively large and costly apparatus to control the stimulus parameters of wavelength, intensity, temporal pattern, and size, as well as projection lenses to project the stimulus onto the viewing screen.

Figure 1:
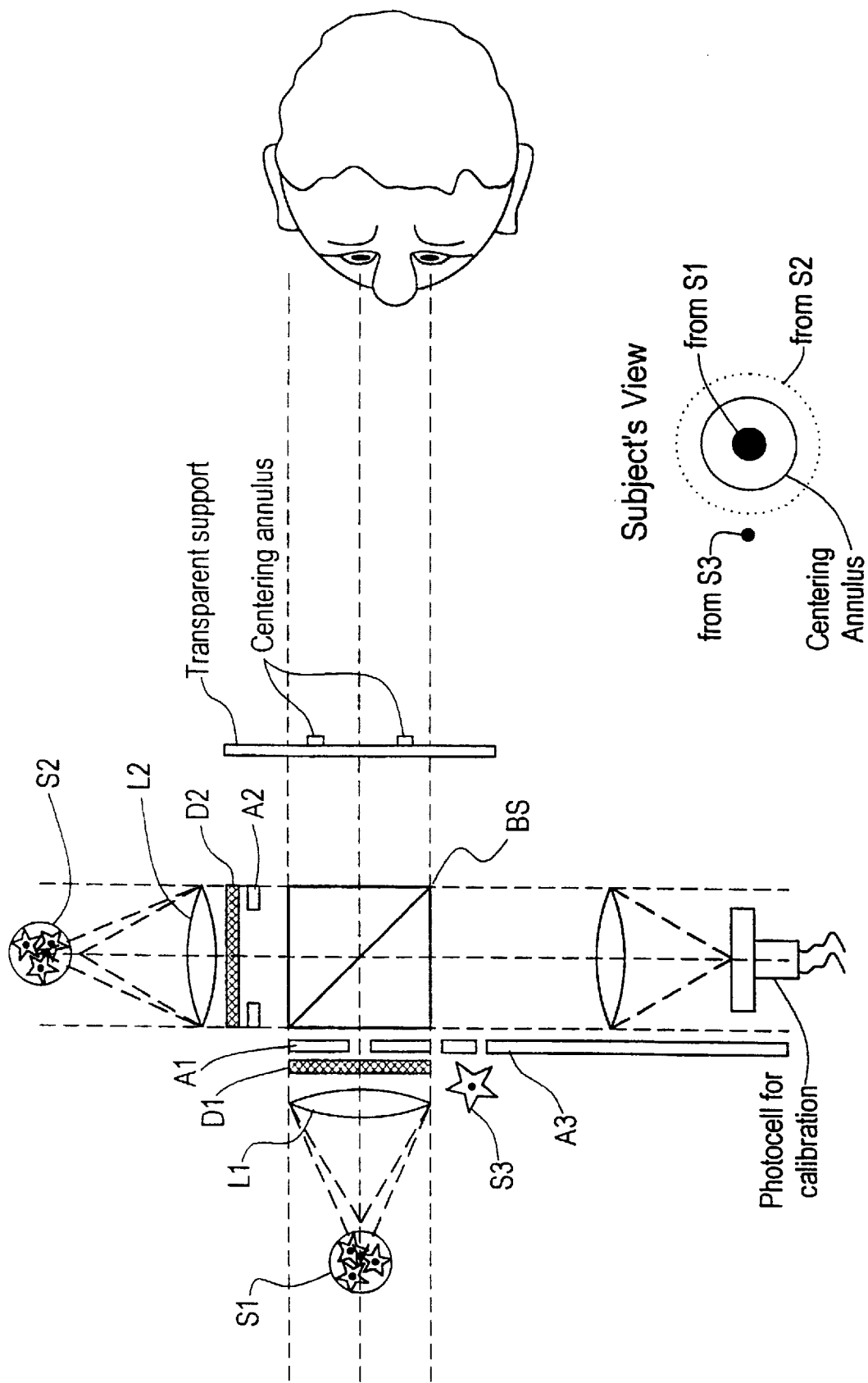
FIG. 1 is a plan view of one embodiment of the apparatus of the invention.

A typical example of the apparatus according to the invention will now be described. Referring to FIG. 1, the light sources (S1–S3) in the apparatus are light-emitting diodes (LEDs). Their light output is controlled electronically by pulse circuits that either are frequency modulated or pulse-width modulated. Their precise emission wavelengths can vary slightly from one production batch to another, and the usual expected values are given here.

Sources S1 and S2 are each composed of three closely juxtaposed LED's for a total of six LED's. the plastic lens that is molded on each LED is removed and the surface is polished. In principle, any combination of six different wavelength bands can be presented to the subject by selecting LED's with different emission spectra. For the determination of macular pigment concentration and for the determination of lens density, peak wavelengths of about 460 nm (blue) and 560 nm (green) are suitable. The control circuitry can energize each LED separately for the measurement of lens density or dark adaptation. Light from the three LED's at S1 is collimated by lens L1 before impinging on a diffuser D1 and being limited to the test stimulus size by aperture A1. For dark adaptation and lens density, a neutral density filter may be inserted between L1 and D1 to reduce the intensity of the light by optical means, so that very dim stimuli can be produced and a wide dynamic range achieved. The light then passes through a beamsplitter (BS) that reflects a small amount of the light to a photocell for calibration. The subject views the test stimulus through the beamsplitter using a centering annulus to position the head so that the eye is aligned with the instrument. For dark adaptation and lens density, A1 is selected to be abut 3 deg of visual angle, and the subject looks at a small fixation point created by aperture A3 that is illuminated by another LED, S3, which emits light of longer wavelengths. The dim fixation point is on steadily and is separately controlled by the electronics. The test stimulus is flashed for about 200–300 msec every 1.5–2 sec. For lens density measurements, it is typically placed 8 deg from the center of the test stimulys. Each time the stimulus is flashed, an auditory cue can be presented to aid the subject. The sources at S2 are not illuminated for measuring lens density.

For measurement of macular pigment density, source S1 is composed of two blue LED's and one green LED. The blue LED's are energized together and alternately with the green LED at frequencies of about 10–18 Hz to create a small flickering target. The diameter of this target is determined by A1 and is usually a disk subtending 1 deg or less of visual angle, but may have other configurations such as an annulus.

Figure 2:
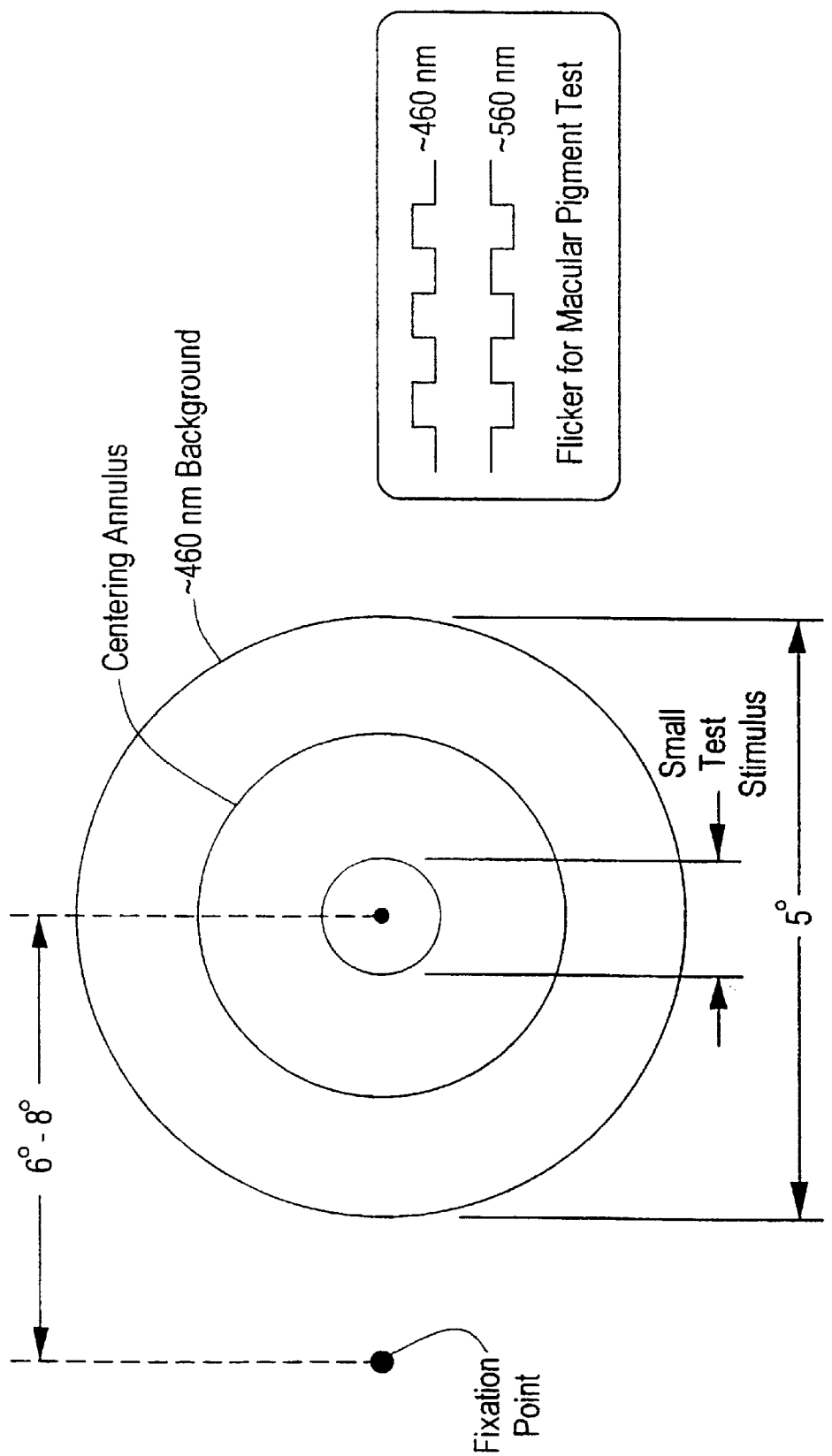
FIG. 2 shows a typical test field as seen by the subject using the embodiment of FIG. 1.

The view seen by the subject is further illustrated in FIG. 2. A background field reflected from the beamsplitter is illuminated by source S2, which is composed of three blue LED's with a peak emission of about 460 nm (blue). Light from S2 is collimated by lens L2, diffused by diffuser D2 and the background field that is created is limited by aperture A2. The background field is steadily illuminated and is designed to produce a retinal illuminance of about 2.2 log Td, which is similar to the light levels used in the prior Maxwellian view systems [45]. To reach these relatively high levels, the diffusers D1 and D2 are selected to be high efficiency. In the current prototype, they are holographically generated light-shaping diffusers that disperse light forward through about a 25 deg angle.

When making the minimum flicker setting in the fovea, the subject looks directly at the test stimulus. To assist the subject in maintaining accurate direction of gaze, a small black dot may be added to the center of A1 or D1. When making the minimum flicker setting in the parafovea, the subject looks at the fixation point created by S3 and A3, which is usually placed about 6 deg from the center of the test stimulus. For subjects with very high macular pigment densities, the fixation point may be placed further peripherally to establish a better baseline value.

In use of the device, the test stimulus is a small diffusing screen that is imaged on the retina by the subject's own eye. All the optical elements are contained in a small box into which the subject looks while having the head comfortably positioned and supported by a chin and forehead rest. For lens density measurements, the subject sees a fixation point and a peripheral stimulus that is briefly flashed. For macular pigment measurements, as shown in FIG. 2, a subject is presented with a constantly illuminated background color at 460 nm in the center of which is a variable colored light source flickering on and off at a frequency lower than the flicker fusion frequency. To make a minimum flicker setting, the subject turns a knob connected to the electronic control box that controls the output of the blue LED at S1 in logarithmic fashion. When the appropriate setting is found, the subject can press a button that signals the experimenter or a computer to record the value. The experimenter or the computer then turns the knob to an unpredictable position before the next trial is run. Measurement of macular pigment is made by determining the energy of the light at the point when the perception of flicker is a minimum or absent. The energy of the flickering light at the point of minimum flicker is related to the amount of light absorbed by the macular pigment lying between the subject's photoreceptors and the light Approximate dimensions of a typical device that can house the apparatus of the invention are 7" wide by 6" high by 24" long, exclusive of power supply, cords, and control cables.

USE

Psychophysical Measurement of Lens Optical Density

A wide body of evidence has shown increasing visual impairment as a function of age [13]. For most people, this visual disability is primarily due to increased OD of the crystalline lens [14,15]. A dense lens is particularly pernicious when optimal vision is required in dim light, such as driving a vehicle at dusk [13,16]. In addition to affecting visual performance by decreasing the amount of light reaching the retina, a dense lens also increases forward scattering of light, which reduces contrast by producing a veiling illumination over retinal images [17].

Age-related cataracts develop slowly over a lifetime and epidemiologic studies that focus only on patients with well-established cataracts may miss factors important in the early development of cataract. Information is needed regarding changes in the lens that begin the process of loss of transparency but precede frank cataract. Lenticular transparency is the result of the short-range order of crystallin proteins [18]. Modification in the ordering of these proteins causes reduced transparency, resulting in higher OD. One type of disruption is aggregation and insolubilization of crystallin proteins, which is considered a primary event in the development of cataract [19]. Mota et al. (1992) [20] have shown that lens OD measured in vivo is highly correlated with the accumulation of these protein aggregates.

In addition to morphological changes, age-related changes in lens physiology also occur and can be tracked by monitoring lens OD. For example, lens membrane potential and resistance decreases with age, while Na+ and free Ca2+ content within the lens increases [21]. Such changes are thought to signal approaching cataract since they are most extreme in the cataractous lens [22,23]. Duncan et al. (1989) [21] have shown that these changes in cation concentrations are well correlated with in vivo measurements of lens OD.

The combination of evidence suggests that measurements of lens OD early in life may signal important changes in the health of the lens.

Although no longitudinal data are available showing that increased lens OD early in life predicts risk for later cataract development, cross-sectional data indicate this possibility. For example, Sample et al. (1988) [24] have shown that the lens OD of individuals with cataract is higher than lens OD of age-matched individuals who do not have cataract. Moreover, diabetics, who have a higher risk of developing age-related cataract than normal individuals [25], also have higher than average lens OD prior to developing cataract [26–29]. In fact, cataract classification systems (e.g., densitometric analysis of Scheimpflug photography; autofluorophotometry) often use high lens OD to establish cataractous status. For example, cataract has been quantified by measuring back-scattered light [30]; a method that is significantly correlated (p<0.001) with psychophysical measurements of lens OD [31]. Cataract has also been quantified by Scheimpflug photography [32], which is also significantly correlated (p<0.001) with psychophysical measurements of lens OD [33].

To measure the OD of the lens, we take advantage of the fact that the dark-adapted (scotopic) sensitivity of aphakic observers whose lens has been surgically removed is determined by the visual pigment of the rod photoreceptors, rhodopsin [34]. Thus, deviations from the rhodopsin spectrum in the scotopic sensitivity of individuals with an intact lens are due primarily to the OD of the lens. Ex vivo data suggest that most of the variation in relative OD with wavelength is due to the properties of the lens nucleus [35]. Lens OD is greatest at short wavelengths and it increases with aging, although for normal subjects the OD at long wavelengths remains low at all ages [36]. Lens OD can therefore be estimated by selecting as a reference a long wavelength light where lens OD is minimal, and comparing the sensitivity of the observer at that reference wavelength to the sensitivity at shorter wavelengths. Because the OD of the lens as a function of wavelength has been well established [36–38], the measurements need only be made at a few wavelengths to estimate the full curve. The correlation between lens OD measured in the left and right eyes is relatively high, r=0.75, p<0.01 [24], so measurements of one eye are an adequate indicator of lens status for most people.

The selection of the reference wavelength is dependent upon two factors. The reference wavelength needs to be long enough so that the OD of the lens is minimal, yet short enough to minimize the possibility that cone photoreceptors will contribute to detection of the stimulus. The peak sensitivity of rods (ca. 500 nm) occurs at shorter wavelengths than the peak sensitivity of the major cone types (ca. 540–570 nm). Thus, as the wavelength of the reference is increased, lens OD is minimized, but the risk that cones will contribute to the measurement increases. As a compromise, we have used 550 nm as our reference wavelength [9]. This choice accepts a small amount of lens OD at the reference wavelength [36] and hence slightly underestimates total lens OD. If a longer wavelength is chosen as reference, a control experiment should be conducted to ensure that only rods are contributing to detection of the stimulus.

The period when rods control the sensitivity of the subject can be identified by tracking the time course of dark-adaptation using the reference wavelength. In brief, subjects are exposed to an intense (about 5 log Tds) broad band light for about two minutes, followed by repeated threshold measurements obtained as rapidly as possible. This can be done by using experienced subjects who adjust the intensity of the test stimulus themselves. Once a smooth dark adaptation curve is obtained, a curve with two time constants should be obtained with a break indicating the transition from cone vision to rod vision at around six minutes (See examples in Wyszecki and Stiles [11], pp 519–520). This control experiment demonstrates that the rods are controlling visual sensitivity under the conditions of the experiment, and also ensures that enough stray light has been eliminated so that true scotopic thresholds are obtained. Note that stimulus size and location on the retina also influence the probability of detection by rods vs cones, so the effects of any changes in those parameters must also be checked by this type of control experiment.

When selecting wavelengths at which to measure lens OD, several points need to be considered. Because the OD of the lens is inversely related to wavelength, the experimenter can maximize differences among subjects by using short wavelengths. This consideration is of particular importance when measuring the lenses of subjects with minimal OD, such as adolescents. Typically a limiting factor when using shorter wavelengths is the energy output of most optical systems. Given the relatively low sensitivity of the visual system from 400–440 nm and the high OD of the lens in older subjects at these wavelengths, relatively high energy is required if a wavelength near 400 nm is selected as the measuring wavelength.

Another consideration is ease of computing lens OD. If the reference wavelength and the measuring wavelength are selected to be at equal absorption values on the rhodopsin curve, then the difference between the two can be taken directly as due to lens OD without referring to the rhodopsin curve itself. Sample et al. (1988) [24] have used a reference wavelength of 560 nm and a measuring wavelength of 410 nm for this purpose. If optimal accuracy is desired, measuring additional wavelengths allows individual spectra to be checked against standard, age-referenced, spectral density curves [11,17,37].

Because of the changing shape of the density spectrum of the lens for older individuals, and the wide variation in lens OD throughout life, measurements designed to correct for prephotoreceptor filtering should be done at the wavelengths of most interest. For example, if an investigator wishes to determine how much light reaches the retina at specific wavelengths, such as the absorption peaks of specific cone types [39], the data are most precise if OD at the wavelength of interest is measured rather than computing interpolated values from other wavelengths using a standard spectral curve of lens OD [11].

The task is explained using suprathreshold stimuli before the subject is given 30–40 minutes of dark adaptation. About 95% of fully dark-adapted sensitivity is reached by this time. During testing, subjects are instructed to stare directly at a small (~20 min), illuminated fixation point that can be located 6–8 degrees eccentric to the test stimulus. It is important to remind subjects frequently to maintain fixation and not to look directly at the test stimulus so that the test stimulus falls outside the retinal region with the highest number of cones and is detected by rods. The size of the test stimulus is typically 2–3 degrees (i.e., large enough to be detected easily with peripheral vision). A check that subjects are detecting the stimulus with their rods may be incorporated by asking subjects to report the color of the test flash. Near threshold, subjects should report that the test flash appears colorless.

A quantitative measure of the absolute threshold of each subject to the flashed test stimulus can be obtained using a variety of techniques. In a typical protocol, subjects are warned of a coming test flash by the experimenter. The test stimulus is then flashed for 500 msec or less, and the subject indicates whether it was seen or not. The intensity of the flash is varied progressively in 0.05 log increments or decrements over a 1.5 log unit range (method of limits) or the intensity is randomly varied within a fixed range (method of constant stimuli). The percentage of time the subjects report seeing the test flash can be plotted against intensity to produce a psychometric function. Absolute thresholds are then defined as the intensity at which the flash is seen 50% of the time. Although reasonably accurate, this process is fairly slow.

We have found that a more expeditious method is to present the subject with the flashing test stimulus repeatedly (e.g., in 300 msec exposures at 1.5 sec intervals) and then allow the subject to identify the intensities where the stimulus is visible 100% of the time, none of the time, and half the time. The subject's performance is aided by providing an auditory cue each time the stimulus is flashed. With this procedure, the entire range from 100% detection to 100% nondetection is typically limited to about 0.5 log units, and the subject is able to estimate the 50% detection value with good reliability. For example, when five repeat determinations are made, the standard deviation of the threshold is about 0.08 log units at 550 nm and about 0.15 log units at 410 nm.

After the psychophysical session, the energy of each stimulus wavelength should be measured (e.g., in nanowatts) using a calibrated photocell, such as shown in FIG. 1.

Psychophysical Measurement of Macular Pigment Optical Density

The ability to measure MP density by psychophysical methods is dependent both upon its spatial distribution and its spectral absorption characteristics. The density of MP is greatest at the fixation locus and declines approximately exponentially with eccentricity to a baseline at about 6–8 deg eccentricity where it is no longer optically detectable [44,45]. To a first approximation, nutritional and environmental influences probably affect the entire pigment distribution, either increasing or decreasing the OD [7]. For most purposes, it is therefore only necessary to determine the OD at the fixation locus relative to the baseline at an eccentric location. If a more detailed spatial profile of pigment density is desired, then separate determinations must be made at additional retinal locations as described elsewhere [45].

The basic approach is to present a small test stimulus that alternates between a wavelength absorbed by MP and a wavelength outside the MP absorption band. For best signal to noise ratio, the stimulus alternates between 460 nm (blue) at the wavelength of maximal absorption of MP and 550–560 nm (green) which is a reference wavelength that is not absorbed by MP. To the subject, this alternating stimulus appears as a small flickering light. The subject is given control of the intensity of the blue light and the subject's task is to adjust it to minimize the flicker. Settings are made at two retinal loci, one at the reference locus of 6 deg eccentricity (the parafovea), and one at the fixation locus (in the fovea). The energy of the blue light necessary to minimize flicker at the fixation locus minus the energy needed in the parafovea is a measure of the density of MP.

To avoid response bias, the experimenter sets the intensity of the blue light to an unpredictable value before each trial. Because of the rapidity of the stimulus flicker, the subjects can not easily judge the amount of the offset and they must attend to the flicker instead of attempting to repeat some 'desired' brightness setting. Five trials at each retinal location are averaged for each data point.

One determinant of task difficulty for naive or elderly subjects is the size of the test stimulus. Most subjects find the task comfortable with test stimuli 0.75 to 1 deg in diameter. The small test field is superimposed on an intense blue (460 nm, 2.2 log troland or brighter) background about 10 deg in diameter for reasons described later. The green reference stimulus that alternates with the blue test stimulus is set to a constant value that provides a retinal illumination of 2.6 log Td. This value was selected to be 1 log unit above the threshold for detection of the green stimulus when it is flickered alone on the blue background at 1 Hz.

The subject only has to attend to the small flickering stimulus; the larger background is constant throughout the measurement. To set the minimum flicker at the fixation locus, the subject looks directly at the test stimulus. To make the baseline determination in the parafovea, the subject looks at the fixation point at the left edge of the field, which places the flickering test stimulus at an eccentric location. The subject then must make the settings for minimum flicker while paying attention to the test stimulus but not looking directly at it.

For some subjects chromatic aberration of the eye causes slight differences in the position or size of the blue and the green test stimuli, so that it is impossible to eliminate flicker in the narrow arcs where the two stimuli fail to superimpose. Usually the chromatic aberration is just a minor nuisance, however, and does not prevent the subject from successfully executing the task.

The absolute intensity of the test stimulus is not critical because the measurement is a comparison between values obtained at two loci on the retina. As a result, moderate differences in lens OD between subjects have no effect because the MP density value for each subject is derived from the difference between two loci on the retina. The contribution of the lens is the same at the two retinal loci, so it is eliminated by taking the difference.

Because thresholds for critical flicker frequency vary with age and other factors [48], appropriate frequencies of alternation of the colors of the test stimulus must be chosen for each individual. Choice of the best temporal frequency is the most challenging part of the procedure for the experimenter. When the conditions are properly chosen, subjects should perceive distinct changes in the degree of flicker as they vary the energy of the blue light. Ideally there should be a narrow range of settings that correspond to minimum flicker, which we call the null range. If the flicker rate is too low, the null range will be very broad, the subject's settings will have high variance, and the precision of the measurement will be poor. If the flicker rate is too high, no setting produces strong flicker, causing the subject to have difficulty locating the null region, again resulting in variable settings. The maximum flicker rate we have used for both fovea and parafovea is 18 Hz, and the minimum rate is 10 Hz.

For most people, it is useful to demonstrate the variation of flicker strength with the energy of the blue is light by starting with the parafoveal measurement using 12 Hz alternation. If the subject continues to see no flicker over a broad range of settings, the flicker rate should be raised until the null range is sufficiently narrow to produce settings of acceptable variance. At the correct flicker rate, it should be possible for the subject to adjust the energy of the blue test light to achieve a complete null, that is, the perception that flicker has ceased entirely. Either increasing or decreasing the energy of the blue light from this null point should cause perception of increased flicker.

Some subjects who have very steady eye position experience perceptual fading of the parafoveal stimulus, which confuses them and makes determination of the flicker null difficult. To avoid this problem it is useful to remind subjects to blink at a normal rate and it may be helpful to periodically turn the test stimulus off entirely. To be sure that the subject has not confused fading of the stimulus with a flicker null, we ask the subject to rate the flicker magnitude, from 0 for no flicker to 10, lots of flicker. Then the subject takes a rest without changing the settings. We resume testing and ask the subject to rate the flicker again with the same settings. If the flicker now appears much stronger, it suggests that fading had occurred or the subject simply became fatigued and the setting needs to be redone.

Once the subject is able to make reliable settings for the parafoveal location, the foveal measurement can be added. Usually the flicker rate for the foveal determination can be around 15 Hz or higher. In the fovea, the fact that MP declines so rapidly with eccentricity means that the amount of flicker at different points within the test stimulus can be different. Consequently, the null may not be complete, but a clear range of minimum flicker is nevertheless attainable. One cue that sometimes helps the subject is the occurrence of an apparent shift in the flicker frequency when approaching the minimum. In a narrow zone around the null point, the stimulus appears to flicker more rapidly, even though the actual flicker rate has not changed. This is apparently a sign that the stimulus is activating only a subset of the visual neurons and the setting is close to the point of minimum flicker.

From our experience, we estimate that 95% of healthy adults can successfully measure their own MP. Nevertheless, this is a foreign experience for most people, and one must always be alert to the possibility that the subject is doing the task incorrectly. In particular, if data show extreme values or high variability, it is prudent to check that subjects are doing the task correctly. One way to check this is to change the wavelength of the test stimulus. The settings should change by the amount predicted by the absorbance spectrum of MP. For example if the 460 nm test is replaced by a 500 nm test, the measured OD should decrease by about 45%. If the wavelength can not easily be changed, then the size or configuration of the test stimulus can be changed instead. The dependence of MP density on test stimulus geometry can be predicted from published data [45].

For subjects in past studies the standard deviation of MP density from repeat sessions with well-motivated subjects was 0.05–0.08 absorbance units [45,49]. Thus, the variability from session to session for a given subject is small compared to the range of MP across subjects, which can be more than 1.0 absorbance units [8,50]. Furthermore, with practice the variability of subjects' settings decreases, so long-term studies could be conducted with greater precision.

Psychophysical methods for measuring MP density are based on the crucial assumption that the foveal patch of retina underlying the pigment has the same relative spectral sensitivity as the parafoveal patch of retina that provides the baseline value. This means that the ratio of the sensitivity to blue light to the sensitivity to green light should be the same at the two retinal loci. This does not require the same absolute sensitivity to light at different retinal loci. Even so, it is not a trivial condition to satisfy, because neural organization varies dramatically with distance from the center of the fovea.

For normal observers, the retinal photoreceptors consist of the rods and three cone types whose responses peak in the short-, middle-, and long-wavelength parts of the visible spectrum. Two of these four types of photoreceptors, the rods and the short-wave-sensitive cones, are known to be distributed in a very nonuniform manner [51,52]. However, the long-wave- and mid-wave-sensitive cones are present in a fairly constant ratio across the central retina [53]. Thus our strategy is to establish stimulus conditions that minimize the contributions of the rods and the short-wave cone system to the flicker determinations, while favoring detection by the mid- and long-wave cone systems.

To minimize the contribution of the short-wave cone system and the rods to the flicker determinations, the wavelength of the background adapting field is selected to be more strongly absorbed by those photoreceptors than by the mid- and long-wave cone systems. In addition, the flicker rate is a temporal frequency near the fusion frequency for the short-wave cone system, but well below fusion frequency for the mid- and long-wave cone systems [54]. Both of these factors contribute to accomplishing the desired goal of biasing detection toward the mid- and the long-wave cone systems.

The following example is presented to illustrate the advantages of the present invention and to assist one of ordinary skill in making and using the same. This example is not intended in any way otherwise to limit the scope of the disclosure.

EXAMPLE

Comparison with Physical Method for Measuring Macular Pigment Density

As a first step in validating the device, we compared MP measured in the traditional manner (Maxwellian View) with MP measured using the device of the invention.

Measurement of Macular Pigment Optical Density

Fifteen men and 17 women (age range, 16–72 yrs) were measured using the two different MP measurement techniques. The ordering of the measurements was counterbalanced in order to avoid possible order effects. All measurements were made in the right eye only. Twenty-eight of the subjects had never participated in a psychophysical task prior to this study and were experimentally naive. The remaining four subjects were experienced in psychophysical tasks and were aware of the purpose of the study. Since this study involved direct comparisons between two methods, no exclusion criteria were used in sample selection. As indicated in Table 1, three subjects had severe cataracts (nuclear and mixed) and were scheduled to have these cataracts removed soon after the MP measurements were performed. Informed consent was obtained from all subjects.

TABLE 1

Descriptive statistics; current smokers (CS); never smokers (NS); past smokers (PS).

| Subject | Iris Color | Age | Sex | MPOD Newt. | MPOD Maxwell | OD Change | Smoking Status | Lens OD Status |
|---------|------------|-----|-----|------------|--------------|-----------|----------------|----------------|
| WR | Brown | 57 | M | 0.12 | 0.15 | −0.03 | CS | Cataract |
| PJ | Black | 23 | M | 0.39 | 0.46 | −0.07 | NS | |
| AT | Blue | 24 | F | 0.34 | 0.46 | −0.12 | NS | |

TABLE 1-continued

Descriptive statistics; current smokers (CS); never smokers (NS); past smokers (PS).

| Subject | Iris Color | Age | Sex | MPOD Newt. | MPOD Maxwell | OD Change | Smoking Status | Lens OD Status |
|---|---|---|---|---|---|---|---|---|
| RC | Brown | 30 | F | 0.42 | 0.505 | −0.09 | NS | 1.69 |
| HJ | Blue | 22 | M | 0.32 | 0.38 | −.06 | NS | 1.5 |
| ML | Black | 48 | F | 0.39 | 0.32 | 0.07 | NS | |
| HC | | | M | 0.11 | 0.02 | 0.09 | | |
| WA | Brown | 25 | M | 0.46 | 0.47 | −0.01 | NS | 1.63 |
| BA | Brown | 31 | F | 0.07 | 0 | 0.07 | NS | 1.37 |
| BG | Blue | 49 | M | 0.065 | 0.17 | −0.11 | CS | Cataract |
| ZL | Black | 30 | M | 0.47 | 0.41 | 0.06 | PS | |
| VM | Brown | 23 | F | 0.314 | 0.25 | 0.06 | NS | 1.51 |
| VN | Brown | 16 | F | 0.27 | 0.22 | 0.05 | NS | |
| RC | Brown | 41 | F | 0.219 | 0.178 | 0.04 | PS | |
| HR | Green | 34 | M | 0.43 | 0.42 | 0.01 | NS | 1.65 |
| LM | Brown | 30 | M | 0.223 | 0.2 | 0.02 | NS | 1.46 |
| GA | Blue | 31 | M | 0.103 | 0.03 | 0.07 | NS | |
| SJ | Blue | 28 | M | 0.19 | 0.15 | 0.04 | NS | |
| TM | Brown | 23 | F | 0.15 | 0.13 | 0.02 | NS | |
| BB | Blue | 58 | F | 0.222 | 0.214 | 0.01 | NS | |
| KM | Brown | 28 | M | 0.164 | 0.111 | 0.05 | NS | |
| RB | Blue | 33 | M | 0 | 0.03 | −0.03 | CS | |
| TC | Brown | 51 | F | 0.188 | 0.142 | 0.04 | PS | |
| MM | Hazel | 49 | F | 0.292 | 0.267 | 0.03 | PS | |
| WB | Brown | 56 | M | 0.595 | 0.594 | 0 | NS | |
| RR | Brown | 29 | M | 0.59 | 0.55 | 0.04 | CS | |
| CF | Blue | 72 | F | 0.01 | 0.06 | −0.05 | NS | Cataract |
| WA | Green | 51 | F | 0.24 | 0.3 | −0.06 | NS | 1.64 |
| AT | Brown | 29 | F | 0.02 | 0 | 0.02 | NS | |
| SS | Blue | 20 | F | 0.17 | 0.19 | −0.02 | NS | 1.1 |
| BJ | Hazel | 21 | F | 0.12 | 0.12 | 0 | NS | |
| VJ | Green | 60 | F | 0.141 | 0.138 | 0.00 | N | |
| Mean +/− SD | | | | 0.244+/− 0.16 | 0.239+/− 0.17 | 0.004+/− 0.01 | | |

Procedure

The procedure for measuring MP was the same whether measured in Maxwellian or Newtonian view. In brief, spectral sensitivity was measured using the light that is maximally absorbed by MP, 460 nm, and light that is not absorbed by MP, 550 or 570 nm. These measurements are made at a retinal locus where MP is the most dense, the center of the fovea, and in an area where MP is minimal and optically undetectable, in this case, 4 or 6 degrees in the temporal retina. Spectral sensitivity is measured using flicker photometry which presents the two test stimuli in a temporal square wave alteration of 12–15 Hz for the foveal condition, and 6–7 Hz in the parafoveal condition. This procedure for measuring MP yields an optical density spectrum for the pigments that matches the extinction spectrum of lutein and zeaxanthin measured ex vivo, as discussed above.

Maxwellian View Measurement

A conventional three-channel Maxwellian view system with a 1000-watt xenon arc light source (Power source: Raytheon Co., Lexington, Mass.; Housing: Kratos Analytical Inc., Ramsey, N.J.) was used for the measurements. The exit pupil of the system was 2 mm. One channel provided a background field, while two other channels were combined to produce a test stimulus. One test channel provided a comparison field whose intensity was adjusted by the subject via a 2.0 log unit circular neutral density wedge in combination with individual neutral density filters (Schott Glass Tech., Duryea, Pa.). The other test channel provided a standard field whose intensity and wavelength composition was constant. The two test channels were presented in square wave alteration for the purpose of flicker photometry. This combination was accomplished by using a sectored, first-surface mirror rotated by a highly regulated Bodine motor (Electro Sales Co., Somerville, Mass.). The wavelength of the comparison test field was produced by a grating monochromator with a nominal half bandwidth of 7 nm (Model H-20, Instruments SA, Inc., Metuchen, N.J.); blocking filters eliminated stray light and higher order spectra. The wavelength of the background and standard test field was produced by Ditric Optics interference filters (bandpass=7 nm). Subjects were positioned for Maxwellian view by using an auxiliary pupil viewer (made with a comparator/reticle used in conjunction with a beam splitter placed immediately before the final focusing lens). Stabilization of the head was maintained by use of an adjustable dental impression bite bar and head-rest assembly.

Stimulus

The circular 1-degree test stimulus was composed of a 2.7 log Td, 550 nm standard field, and a 460 nm comparison field. The intensity of the comparison field was adjusted by the subject. The circular test field was presented near the center of a 10-degree, 2.5 log Td, 460 nm background. A small black dot placed on a slide transparency in the background channel provided a fixation point on the edge of the background in the nasal visual field. This stimulus configuration is shown in FIG. 3B.

Newtonian View Measurement

Figure 3A:
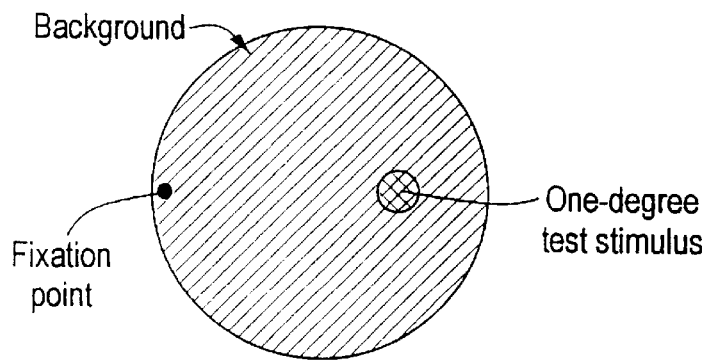
FIGS. 3A and 3B are schematics of the optical system of the invention and stimulus configuration that were used for measuring MP optical density in Newtonian (or natural) view, as described in the Example.
Figure 3B:
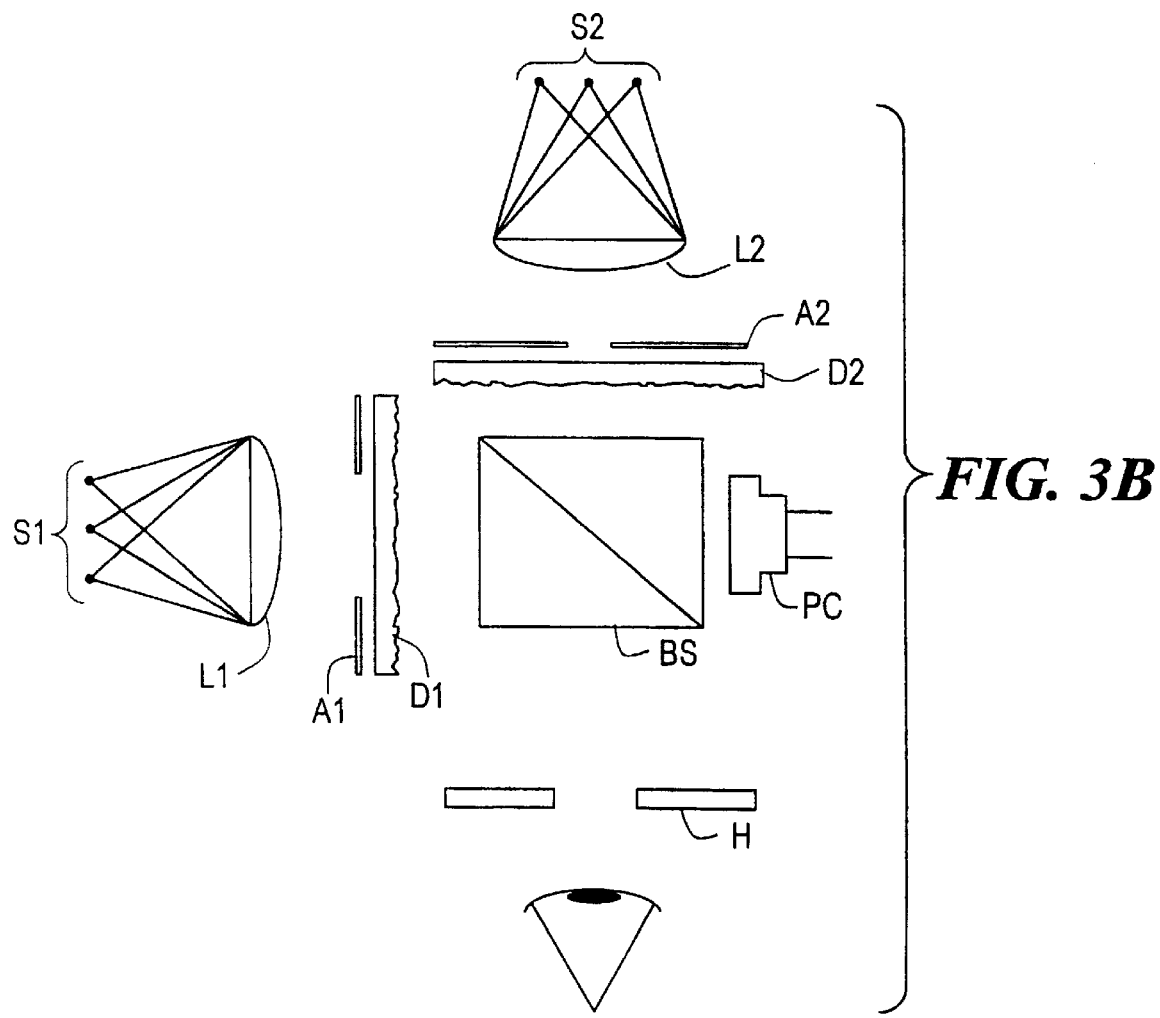

FIG. 3A shows the Newtonian (natural) view optical system used in this study. The light for the background is provided by a source (Si) that consists of three LED's with peak energy at about 470 nm and half-widths of about 20 nm. For the sake of simplicity, S1 is diagrammed as a linear array in FIG. 3A. In actuality, S1 was constructed by packing the three LED's (3 nm in diameter) as tightly as possible in a triangular array. This was done by first grinding off the lens of each LED and then embedding them within a brass tube with an inner diameter of 0.258 filled with an epoxy resin. After curing, the front surface of the resin was ground flat and polished.

Light from S1 was collimated with a planoconvex lens (L1, 10 cm focal length). A 1.75 inch circular aperture (A1), that defined the 6 degree background field, was located approximately 2 inches beyond L1 at a position where collimated light from three LED's overlapped. A1 was constructed by exposing high-density, photographic mylar film with a computer generated image of the aperture. The mylar film was then affixed with optical grade glue to the smooth side of a diffuser, D1. The polycabonate diffuser is a high-efficiency, holographic type (Physical Optics Corporation) with a circular, diffuser angle of 20 degrees. In this example, A1 was viewed by the subject reflected through the diffuser. The subject's eye was located approximately 16 inches from the front surface of the beamsplitter. The entire optical system was enclosed within an opaque, plexiglass box. The subject peered into the system through a 1 inch, circular hole (H) that was centered on the optical axis. The hole was located and sized such that when properly aligned on the optic axis, the subject saw this hole as slightly larger than and concentric with the 6 degree background field.

Light from S2 was collimated with a planoconvex lens (L2, 10 cm focal length). S2 was composed of two LED's with peaks at 458 nm and one with a peak at 570 nm (half-bandwidths of 20 nm). Construction was as for S1. A 0.3 inch aperture (A2), defining the 1-degree test field was placed as for L1. The construction and composition of the aperture-diffuser sandwich was identical to that of the S1 channel. The subject viewed A2 directly through the beamsplitter, which combined the two beams.

When properly positioned, the subject saw the 1-degree superimposed upon the 6-degree background with the slightly larger and out-of-focus edge of the hole (H) concentric with the background. A tiny (5 min) opaque spot was located on the extreme left side of the background to serve as a fixation point for the peripheral condition. Another spot (also 5 min) was located in the center of the target to serve as a fixation point for the foveal condition. The configuration of the stimulus is illustrated in FIG. 3B. Due to the Newtonian view and the 20-degree diffusing angle, head position was not critical. The subject was merely instructed to make sure that the hole was concentric with the background. The 1-degree target was located within the background such that its center subtended a 4-degree angle with respect to the fixation point located on the extreme left. A photocell (PIN-10, UDT Sensors, Inc.) was used to measure the relative radiance of the target and background.

Calibration and Stimulus Control

In preliminary tests we found that the peak spectral energy of individual LED's vary as much as 5 nm within a category defined as the manufacturer's catalogue number. We chose each LED with the desired spectral energy distributions in mind. For the shortwave component of the test field we wanted peak energy to be within 2 nm of 460 nm, which is close to the peak absorption of the macular pigment. The long-wave component of the test field is less critical since the only requirements are that it be in the spectral region beyond the pigments significant absorption (greater than 520 nm) and that it be of reasonable luminance. We chose 570 nm for that value. For the peak energy of the background, we chose a value of 475 nm as the best compromise considering such factors as luminous efficiency and the spectral absorption of rods and short-wave cones. We decided to use a maximum of three LED'S for each source, since a triangular packing gave a good compromise between the desire for maximum radiance and compactness. Thus, we used three LED's (Nichia Corp., Model NSPB300A) for S1, each with peak wavelengths near 475 nm. For the test source, S2, we used two LED'S (Nichia Corp., Model NSPB300A) with peak wavelengths near 460 nm, leaving the third position for the LED peaking at 570 nm. We both test lights are included in one compact source, the necessity of combining them with a light-losing beamsplitter is avoided.

Figure 4:
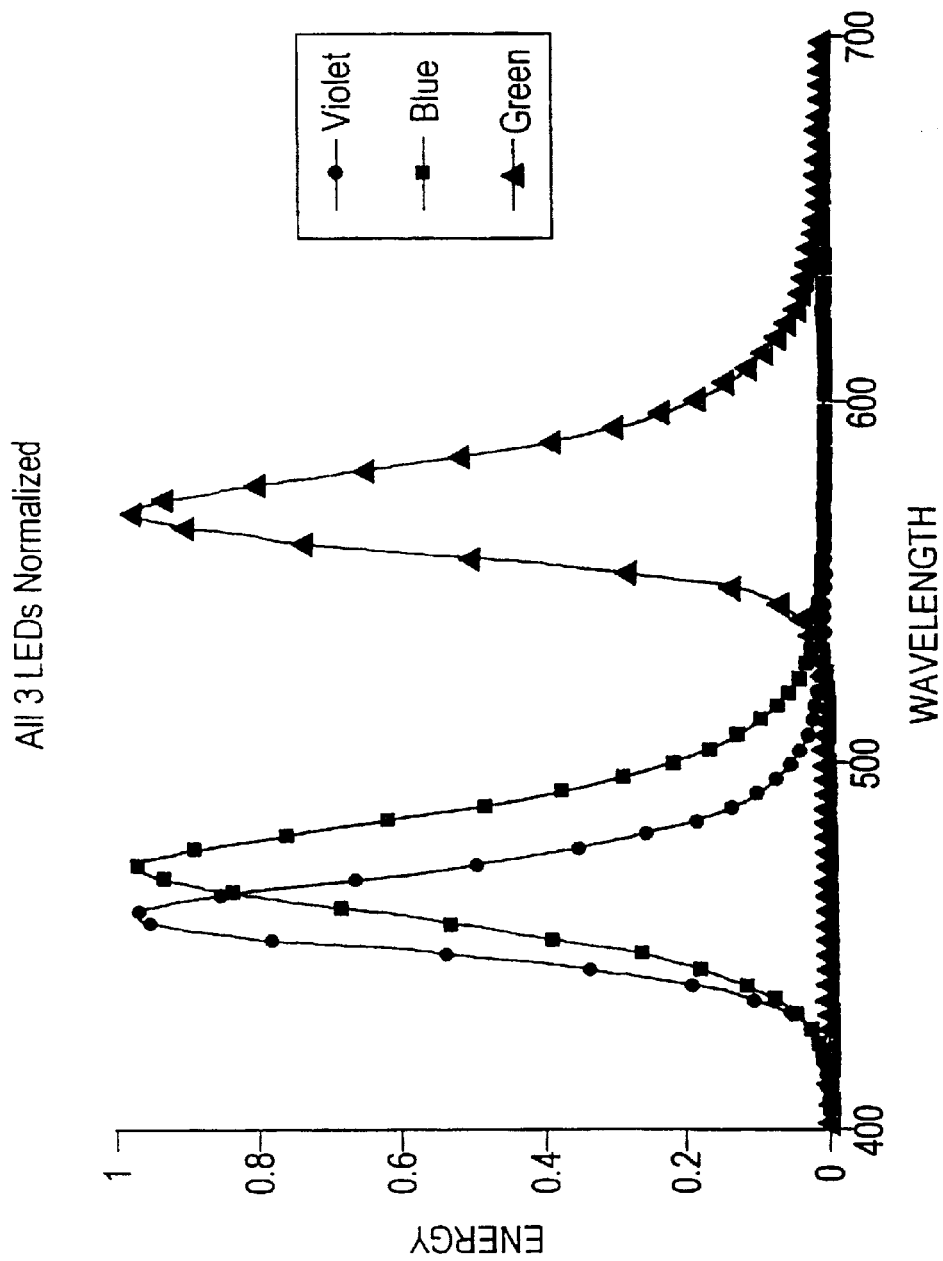
FIG. 4 shows relative spectral energy curve for the LEDs that were used to create the background (squares), measuring (circles) and comparsion (triangles) fields for the measurement of MP in Newtonian view, as described in the Example.

The stimuli was calibrated by placing a spectroradiometer-photometer (model 650, Photo Research) at the eye's position. FIG. 4 shows the relative spectral energy of the background was set at 1.5 log Tds, the highest value that allowed a good adjustment range for the test field. The 570 nm component of the test field was set at 1.7 log Tds, the highest value that allowed a wide range of settings for the 460 nm component. The 460 nm component is, of course, adjusted by the subject to minimize flicker; i.e., it is the dependent variable.

The LED's are driven by constant current supplies. Radiance is controlled by delivering brief (1.5 microsecond), square-wave pulses at a rate that can be varied from approximately 300 Hz to 330,000 Hz. The frequency of each LED is individually adjustable with the radiance levels being monitored by a photocell (PC) and the relative values displayed on a digital display. Thus, the pre-determined radiance values of each field can be precisely set at the beginning of each experimental session. In addition, the radiance of the 460 nm measuring beam can be varied by a current adjustment that allows frequency values to assume absolute radiance values across experimental sessions.

Figure 5:
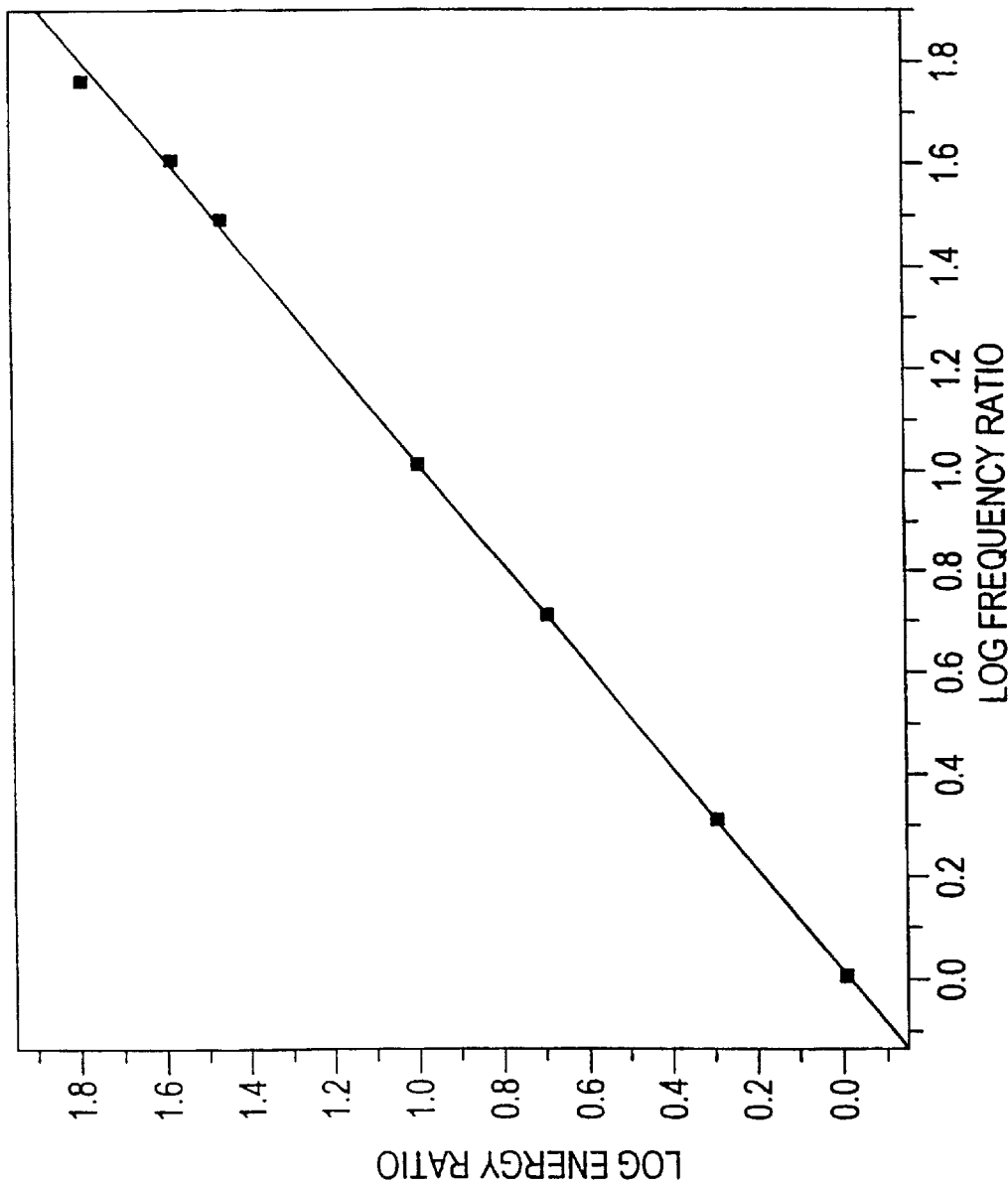
FIG. 5 is a graph comparing the log frequency values with the measured log ratio energy output produced by these changes in frequency.

There is a major advantage of using frequency to control radiance in the particular way that we measure macular pigment density. Our calculation of the pigments optical density is simply:

$$O.D. = \text{Log } 10 \; R_f/R_p,$$

where $R_f$ and $R_p$ are simply the radiances of the 460 nm test beam that results in minimum flicker with respect to the 570 nm standard at the foveal and parafoveal loci, respectively. Since the frequency should be proportional to the radiance with a slope of 1.0 and origin of 0.0, then it follows that:

$$O.D. = \text{Log } 10 \; F_f/F_p,$$

where $F_f$ and $F_p$ refer to the frequency of the 460 nm test beam at the foveal and parafoveal positions, respectively. This is true, of course, only if the individual 1.5 microsecond pulses do not change shape as frequency is varied. We tested this conclusion by placing a radiometer at the eye's position and measuring the actual integrated radiance as frequency was varied over a large range. In actuality, we chose a range that would allow considerable adjustment (about 0.3 log) below and above the lowest and highest values. Thus, the range we explored would be a conservative estimate of a good working region for the measurement of macular pigment. FIG. 5 shows that log energy ratio of the lowest and highest radiance values plotted against the log frequency ratio of the corresponding frequency values. Notice that the data points fall very close to the straight line, which has a slope of 1.0 and an intercept of 0.0. The conclusion is clear that frequency rations can substitute for radiance ratios. This greatly simplifies the use of the instruments since frequency is easily determined with inexpensive and accurate electronic devices, whereas an accurate energy calibration requires a fairly expensive and elaborate analogue device. The use of frequency is a major simplifying aspect of the device.

Measurement of Lens Optical Density

For a subset of subjects (n=10), we also measured lens optical density (see Table 1). Scotopic thresholds were obtained using two channels of the Maxwellian view system. One channel provided a dim, blue, 20-minute fixation point. A second channel provided a 2.8-degree test stimulus. The test stimulus was alternately composed of 410 (high lens absorbance) and 550 nm light (this wavelength was used as a reference and minimal lens absorbance was assumed). These wavelengths were selected because of equal absorption values on the rhodopsin curve. Lens OD was calculated by directly subtracting the log relative sensitivity value at 410 nm from the log relative sensitivity value at 550 nm without referring to the rhodopsin curve itself. Test field exposures were determined by a Uniblitz electromagnetic shutter (Rochester, N.Y.). The test stimulus was always presented at six degrees in the nasal visual field. Scotopic thresholds were obtained after subjects were dark adapted for 40 minutes.

Results

Figure 6:
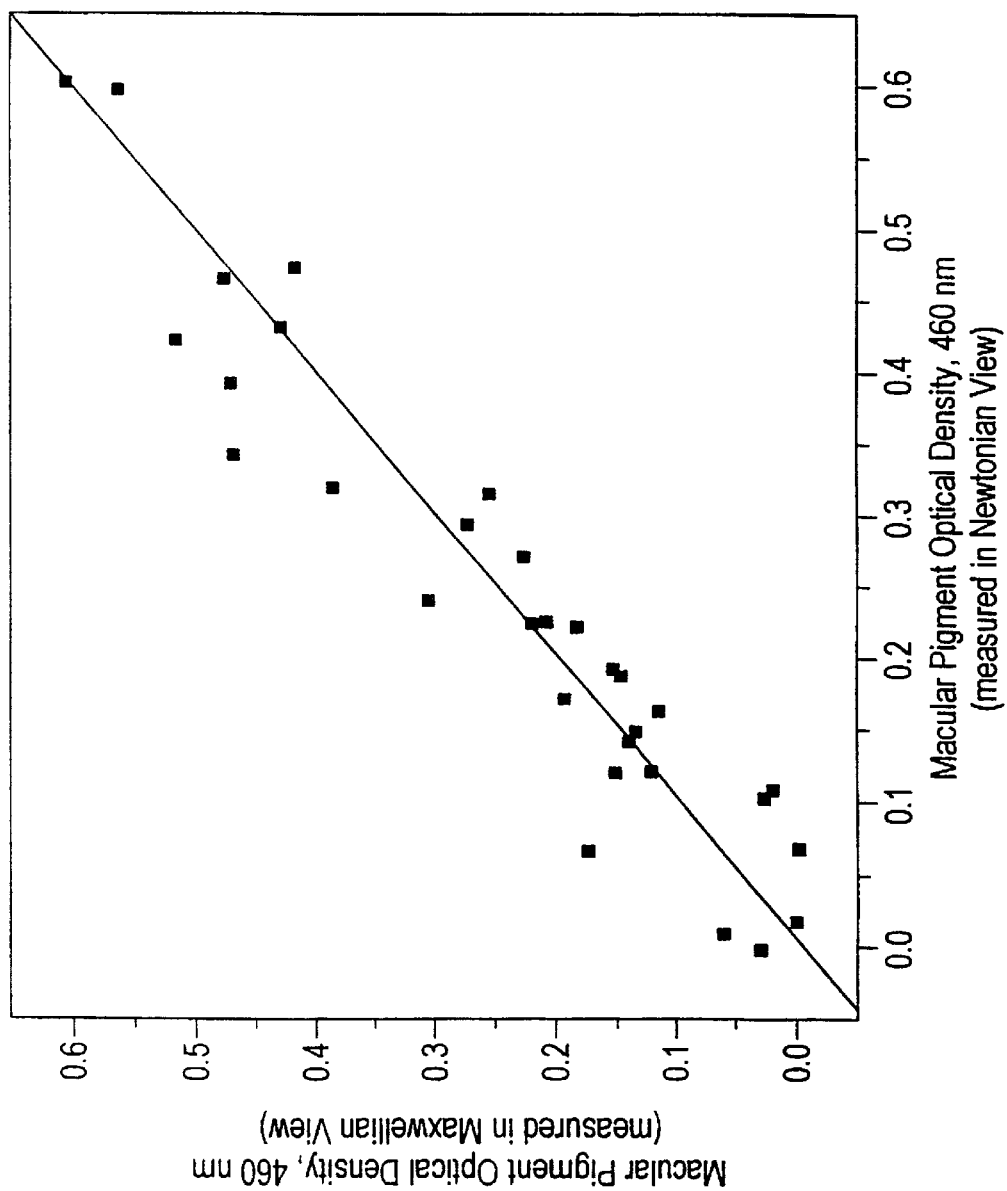
FIG. 6 shows the relationship between MP optical density measured in Newtonian and Maxwellian view, as described in the Example.

MP optical density measured using the Maxwellian system and the Newtonian (natural) viewing systems are presented in Table 1. As shown in FIG. 6, the two methods provide highly similar individual and mean values are highly correlated (Y=0.0+1.0X, r=+0.95). Note that the intercept of the line is zero and the slope is one, showing that there is no systematic difference between the two techniques. In fact, the average absolute change in these values is lower (mean= 0.04, SD=0.03) than reliability values reported for studies that obtained repeated measures using the same method on different days [18]. To obtain a reliability estimate for MP measured in Newtonian view, the MP density of four subjects was measured over a period of two to four weeks. An analysis indicated that the data were reliable (Cronbach's a=0.89).

As shown in the Table 1, differences between the MP values obtained with the two techniques is not related to individual differences in lens density. Moreover, although there were only three patients with cataract, differences in MP density between the two techniques were not exaggerated in these cases. For two subjects we tested the effects of pupil size by measuring MP with the device before and after pupil dilation with a mydriatic. The MP values when measured with nondialated pupils (0.16 and 0.42) were very similar to the values obtained during dilation (0.11 and 0.43, respectively). For two subjects, we also tested the effects of head movements on the MP values obtained using the device. The limiting factor in the lateral direction is the ability to see the stimulus. Basically, a subject can only move approximately 1.5 cm to the right or left before the stimulus is occluded by baffling. When subjects are misaligned this way, however, no differences are found in their MP values (range of differences=0.02). In the Z direction, subjects can move at least 10 cm forward or backward without any change in their MP values(range of differences= 0.04).

Individual differences in the average MP density of the individuals in this small sample tended to be consistent with our past observations on determinants of individual differences in MP density in different populations. For example, the average MP (mean=0.21, SD=0.13, n=17) of the females was lower than the average MP(mean=0.29, SD=0.21, n=15) of the males. The average MP of the smokers (mean=0.20, SD=0.22, n=5) was lower than the MP density of the nonsmokers(mean=0.27, SD=0.17, n=27). Finally, the MP of the blue-eyed subjects(mean=0.17, SD=0.13, n=9) was lower than the MP of the green-hazel eyed subjects(mean= 0.29, SD=0.21, n=5) or the brown-black eyed subjects (mean=0.29, SD=0.19, n=16). Finally, the MP density of those individuals with cataract was low. The sample size of these groups were too small to assess the statistical significance of these differences.

Utilization of the In Vivo Measurements

Age-related macular degeneration (AMD) and cataract are conditions that take many years to develop. Most etiologic studies of these conditions, however, have focused on patients that already exhibit frank clinical symptoms. Yet efforts to prevent loss of visual function must emphasize retarding the aging process that precedes the disease. For preventive approaches to be successful, information from in vivo measurements is needed regarding the status of the lens and the retina before deleterious changes are far advanced and intervention may be too late.

Measurements of lens OD are essential for assessing the impact of nutrition and of lifestyle factors such as smoking and environmental exposures at different times in the lifespan. The results could be used to motivate subjects to change their lifestyle. For example, smokers who learn that they have high lens densities for their age group might feel added motivation to stop smoking in order to avoid cataract.

Because the psychophysical measurements are nontraumatic they can be repeated as frequently as needed to follow changes over time. Cross-sectional data on lens OD as a function of age [9,24,38,60] suggest that lens OD increases linearly from about 15–20 years, but there is a rapid acceleration in OD changes after age 50. If there are differences in the rate of lens OD changes in younger (<50 yrs) and older (>50 yrs) individuals (as is widely suggested), differences may also exist in their respective risk factor profiles. The factors that may be responsible for the putative acceleration in lens OD changes with age should be investigated by following individual subjects over time. Otherwise, one can not distinguish between a common pattern that occurs in most individuals, and a break point where some subjects suddenly begin to get worse, while others age more gradually.

For older individuals, the lens may absorb and scatter enough light to limit their visual capacities. [15,61] In particular, increased lens OD probably is associated with poorer visual performance in dim light. Thus, lens OD is important to study, not just for predicting possible later disease, but also for understanding its immediate deleterious effects on normal vision. Prevention of visual handicaps due to increased lens density may require modification of unhealthy behavior patterns. To convince people to modify their behavior we need to demonstrate how the health of their lens affects their quality of life.

The fact that MP can be measured psychophysically provides the unusual opportunity to monitor noninvasively the concentration of a nutrient in tissue. By exploiting this opportunity, we have assembled evidence that the MP carotenoids protect against age-related losses in visual sensitivity [39] and age-related ocular disease. MP selectively absorbs "blue" light (ca. 400–500 nm), which is particularly harmful to ocular tissues [62, 63], and the MP carotenoids may have other protective roles as well. [40] Consistent with a protective role for MP, we have found that low MP density is associated with many risk factors for AMD (iris color [64], sex [8], smoking status [65], dietary patterns [8]). A protective role is also consistent with biochemical studies of postmortem eyes showing that MP density is lower in AMD eyes compared to matched controls [66].

Utilization of in vivo measurements of MP might help to resolve some of the inconsistencies in the epidemiologic literature. For example, although some studies have indicated that dietary intake of lutein and zeaxanthin [67], and higher blood concentrations of carotenoids [68], protect against AMD, other studies have not found a relationship [69,70]. However, our data have shown that dietary intake and blood concentrations of lutein and zeaxanthin are only moderately related to retinal concentrations of lutein and zeaxanthin as measured by MP density [8]. The blood-retina relationship is particularly poor for women, who comprise the majority of subjects for most epidemiologic studies of AMD. Moreover, we also showed that, although most subjects respond to increased intake of lutein and zeaxanthin with increases in MP density, a minority did not respond [7]. If lutein and zeaxanthin protect the retina locally, measures of these nutrients in the blood may be imprecise predictors of the state of the retina.

Similar discrepancies between blood and tissue measures of nutrients have been encountered when characterizing the nutritional status of the lens. For example, in the Italian-American Cataract study [71] of risk factors for cataract, the antioxidant status of the lens was characterized by measuring the activity of antioxidant enzymes in erythrocytes. No relationship was found between these measures and cataract risk. A later analysis [72] of the lenses of these same patients, however, revealed that there was no correlation between the erythrocyte measures and the same enzyme activity measured in the lens epithelium.

The uncertainties inherent in using blood values of nutrients to predict tissue status have led us to suggest that measuring MP may provide a more precise estimate of long-term ocular nutritional status. As long as dietary patterns remain stable, MP density remains stable over much of the lifespan [45]. This stability probably reflects the tendency for individuals to maintain the same diet for long time periods [73,74]. When individuals change their intake of dietary carotenoids significantly, however, MP density of most subjects changes in tandem [7]. A generally healthy diet would be indicated by high intake of fruits and vegetables, which is usually associated with high serum concentrations of lutein and zeaxanthin [75], which in turn produces high MP density [7]. In addition high MP density signals the subject's ability to accumulate carotenoids from the diet into the retina.

REFERENCES

1. Boynton, R. M., Vision. In Experimental Methods and Instrumentation in Psychology. Sidowski, J. B., Ed. McGraw-Hill, New York, 1966, pp. 273–330, see especially pp 300–328.
2. Knowles, A. and Dartnall, H. J. A The photobiology of vision. In The Eye, 2nd ed., Vol 2B. Davson, H., Ed. Academic Press, New York, 1977, pp 56–57.
3. Pierscionek, B. K. and Weale, R. A. The optics of the eye and lenticular senescence. Doc. Ophthalmol., 89, 321–25, 1995.
4. Snodderly, D. M., Brown, P. K., Delori, F. C. and Auran, J. D. The macular pigment. I. Absorbance spectra, localization, and discrimination from other yellow pigments in primate retinas. Invest. Ophthalmol. Vis. Sci., 25, 660–673, 1984.
5. Bone, R. A., Landrum, J. T. and Tarsis, S. L. Preliminary identification of the human macular pigment. Vision Res., 25, 1531–1539, 1985.
6. Malinow, M. R., Feeney-Burns, L., Peterson, L. H., Klein, M. L. and Neuringer, M. Diet related macular anomalies in monkeys. Invest. Ophthalmol. Vis. Sci., 19, 857–863, 1980.
7. Hammond, B. R., Johnson, E. J., Russell, R. M., Krinsky, N. I., Yeum, K J, Edwards, R. B. and Snodderly, D. M. Dietary modification of human macular pigment. Invest. Ophthalmol. Vis. Sci., 38, 1795–1801, 1997.
8. Hammond, B. R., Curran-Celentano, J., Judd, S., Fuld, K., Krinsky, N., Wooten, B R and Snodderly, D M. Sex differences in macualar pigment optical density: Relation to plasma carotenoid concentrations and dietary patterns. Vision Res., 36, 2001–2012, 1996.
9. Hammond, B. R., Wooten, B. R., Snodderly, D. M. The retinal carotenoids lutein and zeaxanthin associated with the clarity of the human crystalline lens. Opt. Vis. Sci., 74, 499–504, 1997.
10. Zeffrin, B. S., Applegate, R. A., Bradley, A. and van Heuven, W. A. Retinal fixation point location in the foveal avascular zone. Invest. Ophthalmol. Vis. Sci., 31, 2099–2105, 1990.
11. Wyszecki, G. and Stiles, W. S. Color Science, 2nd ed., Wiley, New York, 1982.
12. Westheimer, G. The Maxwellian View. Vision Res., 6, 669–82, 1966.
13. Kline, D. Light, Ageing and Visual Performance. In Vision and Visual Dysfunction: The Susceptible Visual Apparatus. Marshall, J., Ed. CRC Press, Boca Raton, 1991, pp. 150–161.
14. Mangione, C. M., Phillips, R. S., Seddon, J. M., Lawrence, M. G., Cook, E. F., Dailey, R. and Goldman, L. Development of the 'Activities of Daily Vision Scale.' Med. Care., 30, 1111–1126, 1992.
15. Klein, B. E. K., Klein, R. and Jensen, S. C. Visual sensitivity and age-related eye diseases. The Beaver Dam Eye Study. Ophthal. Epidemiol., 3, 47–55, 1996.
16. Kosnik, W., Winslow, L., Kline, D., Rasinski, K. and Sekuler, R. Visual changes in daily life through adulthood. J. Gerontol. Psychol. Sci., 43, 63–70, 1988.
17. Van Den Berg, TJTP. Depth-dependent forward light scattering by donor lenses. Invest. Ophthalmol. Vis. Sci., 37, 1157–66, 1996.
18. Delaye, M. and Tardieu, A. Short-range order of crystallin proteins accounts for eye lens transparency. Nature, 302, 415–17, 1983.
19. Berman, E. Biochemistry of the Eye. Plenum Press, New York, 1991, pp. 201–274.
20. Mota, M. C., Ramalho, J. S., Carvalho, P., Quadrado, J. and Baltar, A. S. Monitoring in vivo lens changes: A comparitive study with biochemical analysis of protein aggregation. Doc. Ohthalmol., 82, 287–96, 1992.
21. Duncan, G., Hightower, K. R., Gondolfi, S. A., Tomlinson, J. and Mariani, G. Human lens membrane cation permeability increases with age. Invest. Ophthalmol. Vis. Sci., 30, 1855–59, 1989.
22. Duncan, G. and Bushell, A. R. Ion analyses of human cataractous lenses. Exp. Eye Res., 20, 223–229, 1975.
23. Maraini, G. and Mangili, R. Differences in proteins and in the water balance of the lens in nuclear and cortical types of senile cataract. In The Human Lens in Relation to Cataract. CIBA Symposium 19. Associated Science Pub., Amsterdam, 1973.
24. Sample, P. A., Esterson, F. D., Weinreb, R. N. and Boynton, R. M. The aging lens: In vivo assessment of light absorption in 84 human eyes. Invest. Ophthalmol. Vis. Sci., 29, 1306–1311, 1988.
25. Leske, M. C., Chylack, L. T., Wu, S-Y., The Lens Opacity Case Control Study Group. The lens opacity case control study: Risk factors for cataract. Arch. Ophthalmol., 109, 244–251, 1991.
26. Lutze, M. and Bresnick, G. H. Lenses of diabetic patients "yellow" at an accelerated rate similar to older individuals. Invest. Ophthalmol. Vis. Sci., 32, 194–199, 1991.
27. Olbert, D., Hockwin, O., Baumgartner, A., Wahl, P., Hasslacher, C., Laser, H. and Eschenfelder, V. Long-term follow up of the lenses of diabetic patients using Scheimpflug photography linear densitometry. Klinische Monatsblatter fur Augenheilkunde, 189, 363–366, 1986.
28. Cotlier, E. Senile cataracts: Evidence for acceleration by diabetes and deceleration by salicylate. Can. J. Ophthalmol., 16, 113–118, 1981.
29. Hardy, K. J., Scarpello, J. H., Foster, D. H. and Moreland, J. D. Effect of diabetes associated increases in lens O.D. on colour discrimination in insulin dependent diabetes. Br. J. Ophthalmol., 78, 754–756, 1994.
30. Ben-Sira, I., Weinberger, D., Bodenheimer, J. Yassur, Y. Clinical method for measurement of light back scattering from the in vivo human lens. Invest. Ophthalmol. Vis. Sci., 19, 435–437, 1980.
31. Sample, P. A., Quirante, J. S. and Weinreb, R. N. Age-related changes in the human lens. Acta Ophthalmologica, 69, 310–314, 1991.
32. Muller-Breitnekamp, U. and Hockwin, O. Scheimpflug photography in clinical ophthalmology: A review. Ophthalmic Res., 24 (Suppl.), 47–54, 1992.
33. Bosem, M. E., Sample, P. A., Martinez, G. A., Lusky, M. and Weinreb, R. N. Age-related changes in human lens: A comparison of Scheimpf lug photography and lens density index. J. Cataract Refract. Surg., 20, 70–73, 1994.
34. Wald, G. and Brown, P. K. Human rhodopsin. Science, 127, 22–226, 1958.
35. Mellerio, J. Yellowing of the human lens: Nuclear and cortical contributions. Vision Res., 27, 1581–1587, 1987.
36. Van Norren, D. and Vos, J. J. Spectral transmission of the human ocular media. Vision Res, 14, 1237–1244, 1974.
37. Pokorny, J., Smith, V. C. and Lutze, M. Aging of the human lens. Applied Optics, 26, 1437–40, 1987.
38. Johnson, C. A., Howard, D. W., Marshall, D. and Shu, H. A noninvasive video-based method of measuring lens transmission properties of the human eye. Opt. Vis. Sci., 70, 944–955, 1993.
39. Hammond, B. R., Wooten, B. R. and Snodderly, D. M. Preservation of visual sensitivity of older individuals: Association with macular pigment density. Invest. Ophthalmol. Vis. Sci., in press.
40. Snodderly, D. M. Evidence for protection against age-related macular degeneration by carotenoids and antioxidant vitamins. Am. J. Clin. Nutr., 62S, 1448S–1461S, 1995.
41. Werner, J. S., Donnelly, S. K. and Kliegl, R. Aging and human macular pigment density. Vision Res., 27, 257–268, 1987.
42. Snodderly, D. M., Handelman, G. J. and Adler, A. J. Distribution of individual macular pigment carotenoids in central retina of Macaque and Squirrel monkeys. Invest. Ophthalmol. Vis. Sci., 32, 268–279, 1991.
43. Bone, R. A., Landrum, J. T., Fernandez, L. and Tarsis, S. L. Analysis of the macular pigment by HPLC: Retinal distribution and age study. Invest. Ophthalmol. Vis. Sci., 29, 843–849, 1988.
44. Snodderly, D. M., Auran, J. D. and Delori, F. C. The macular pigment. II. Spatial distribution in primate retinas. Invest. Ophthalmol. Vis. Sci., 25, 674–685, 1984.
45. Hammond, B. R., Wooten, B. R. and Snodderly, D. M. Individual variations in the spatial profile of human macular pigment. J. Opt. Soc. Am. A., 14, 1187–1196, 1997.
46. Bone, R. A., Landrum, J. T., Hime, G. W., Cains, A. and Zamor, J. Stereochemistry of the human macular carotenoids. Invest. Optalmol. Vis. Sci., 34, 2033–2040, 1993.
47. Handelman, G. J., Snodderly, D. M., Krinsky, N. I., Russett, M. D. and Adler, A. Biological control of primate macular pigment: Biochemical and densitometric studies. Invest. Ophthalmol. Vis. Sci., 32, 257–267, 1991.
48. Curran, S. Critical fusion flicker techniques in psychopharmacology. In Human Psychopharmacology: Methods and Measures. Vol. 3. Hindmarch, I. and Stonier, P. D., Eds, John Wiley, Chichester, 1990, pp. 21–38.
49. Hammond, B. R. and Fuld, K. Interocular differences in macular pigment density. Invest. Ophthalmol. Vis. Sci., 33, 350–355, 1992.
50. Pease, P. L., Adams, A. J. and Nuccio, E. Optical density of human macular pigment. Vision Res., 27, 705–710, 1987.
51. Curcio, C. A., Sloan, K. R., Kalina, R. E. and Hendrickson, A. E. Human photoreceptor topography. J. Comp. Neurol., 292, 497–523, 1990.
52. Curcio, C. A., Allen, K. A., Sloan, K. R., Lerea, C. L., Hurley, J. B., Klock, I. B. and Milam, A. H. Distribution and morphology of human cone photoreceptors stained with anti-blue opsin. J. Comp. Neurol., 312, 610–624, 1991.
53. Nerger, J. L. and Cicerone, C. M. The ratio of L cones to M cones in the human parafoveal retina. Vision Res., 32, 879–888, 1992.
54. Brindley, G. S., DuCroz, J. J. and Rushton, W. A. H. The flicker fusion frequency of the blue-sensitive mechanism of colour vision. J. Physiolol., 183, 497–500, 1966.
55. Delori, F. C., Goger, D. G., Hammond, B. R., Snodderly, D. M. and Burns, S. A. Foveal lipofuscin and macular pigment. ARVO Abstracts., Invest. Ophthalmol. Vis. Sci., 38, S355, 1997.
56. Bernstein, P. S., Balashov, N. A., Yoshida, M., McClane, R. W. and Gellerman, W. Raman spectroscopy of macular carotenoids in intact human retina. ARVO Abstracts., Invest. Ophthalmol. Vis. Sci., 38, S303, 1997.
57. Kilbride, P. E., Alexander, K. R., Fishman, M. and Fishman, G. A. Human macular pigment assessed by imaging fundus reflectometry. Vision Res., 29, 663–673, 1989.
58. Delori, F. C., Staurenghi, G., Goger, D., Weiter, J. J. Macular pigment density measured by reflectometry and flourophotometry. Noninvasive Assessment of the Visual Ssytem. OSA Technical Digest, 3, 240–243, 1993.
59. Van Norren, D. and Tiemeijer, L. F. Spectral reflectance of the human eye. Vision Res., 26, 313–320, 1986.
60. Coren, S. and Girgus, J. S. Density of human lens pigmentation: In vivo measures over an extended age range. Vision Res., 12, 343–346, 1972.
61. Attebo, K., Mitchell, P. and Smith, W. Visual acuity and the causes of visual loss in Australia, Ophthalmol., 103, 357–364, 1996.
62. Ham, W. T. and Mueller, H. A. Retinal sensitivity to damage by short-wavelength light. Nature, 260, 153–154, 1976.
63. Ham, W. T., Ruffolo, J. J., Mueller, H. A., Clarke, A. M. and Moon, M. E. Histologic analysis of photochemical lesions produced in rhesus retina by short wave-length light. Invest. Ophthalmol. Vis. Sci., 17, 1029–1035, 1978.
64. Hammond, B. R., Fuld, K. and Snodderly, D. M. Iris color and Macular Pigment Optical Density. Exp. Eye Res., 62, 715–720, 1996.
65. Hammond, B. R., Wooten, B. R. and Snodderly, D. M. Cigarette smoking and retinal carotenoids: Implications for age-related macular degeneration. Vision Res., 36, 3003–3009, 1996.
66. Landrum, J. T., Bone, R. A. and Kilbum M. D. The macular pigment: A possible role in protection from age-related macular degeneration. In Advances in Pharmacology. Sies, H. Ed. Academic Press. New York. 1996, pp. 537–556.
67. Seddon, J. M., Ajani, U. A., Sperduto, R. D., Hiller, R., Blair, N., Burton, T. C., Farber, M. D., Gragoudas, E. S., Hailer, J., Miller, D. T., Yannuzzi, L. A. and Willet, W. Dietary carotenoids, vitamins A, C, and E, and advanced age-related macular degeneration. J. A. M. A., 272, 1413–1420, 1994.
68. Eye Disease Case-Control Study Group . Antioxidant status and neovascular age-related macular degeneration. Arch. Ophthalmol., 111, 104–109, 1993.
69. Mares-Perlman, J. A., Brady, W. E., Klein, R, Klein, B. E., Bowen, P., Stacewicz-Sapuntzakis, M. and Palta, M. Serum antioxidants and age-related macular degeneration in a population-based case-control study. Arch. Ophthalmol., 113, 1518–1523, 1995.
70. Mares-Perlman, J. A., Brady, W. E., Klein, R., VandenLangenberg, G. M., Klein, B. E. and Palta, M. Dietary fat and age-related maculopathy. Arch. Ophthalmol., 113, 743–748, 1995.
71. Italian Cataract Study Group. Risk factors for age-related cortical, nuclear, and posterior subcapsular cataracts. Am. J. Epidemiol., 133, 541–553, 1991.
72. Belpoliti, M., Maraini, G., Alberti, G., Corona, R. and Crateri, S. Enzyme activities in human lens epithelium age-related cataract. Invest. Ophthalmol. Vis. Sci., 34, 2843–2847, 1993.
73. Jensen, O. M., Wahrendorf, J., Rosenqvist, A., and Geser, A. The reliability of questionnaire-derived historical dietary information and temporal stability of food habits in individuals. Am. J. Epidemiol., 120, 281–290, 1984.
74. Thompson, F. E., Mezner, H. L., Lamphiear, D. E. and Hawthorne, V. M. Characteristics of individuals and long term reproducibility of dietary reports: The Tecumseh diel: methodology study. J. Clin. Epidemiol., 43, 1169–78, 1990.
75. Martini, M. C., Campbell, D. R., Gross, M. D., Grandits, G. A., Potter, J. D., and Slavin, J. L. Plasma carotenoids as biomarkers of vegetable intake: The University of Minnesaota Cancer Prevention Research Unit Feeding Studies. Cancer Epidemiol. Biomark. Prev., 4, 491–496, 1995.
76. Yeum, K-Y, Taylor, A., Tang, G. and Russell, R. M. Measurement of carotenoids, retinoids and tocopherols in human lenses. Invest. Ophthalmol. Vis. Sci., 36, 2756–2761, 1995.
77. Cornsweet, T. N. Visual Perception. Academic Press, New York., 1972.
78. Harrington, D. O. The Visual Fields: A textbook and atlas of clinical perimetry. Mosby, St. Louis, 4th Ed., 1976.
79. Hammond, B. R., Wooten, B. R., Snodderly, D. M. Individual variations in the spatial profile of macular pigment. JOSAA. 14:1187–1196 1997.

While the present invention has been described in conjunction with a preferred embodiment, one of ordinary skill, after reading the foregoing specification, will be able to effect various changes, substitutions of equivalents, and other alterations to the compositions and methods set forth herein. It is therefore intended that the protection granted by Letters Patent hereon be limited only by the definitions contained in the appended claims and equivalents thereof.

What is claimed is:

1. An apparatus for psychophysical determination of an ocular component in an eye of a test subject, said apparatus comprising:
   a light source comprising at least one electronically controlled, light-emitting element wherein the output of said light-emitting element can be varied electronically by said test subject;
   control circuitry for energizing said light-emitting element;
   an aperture for presenting a test stimulus from said light-emitting element to a test subject; and
   a head positioning device for aligning an eye of a test subject in a position to view said test stimulus.

2. The apparatus of claim 1, wherein said light-emitting element is a light-emitting diode.

3. The apparatus of claim 1, wherein said light source comprises at least two electronically controlled, light-emitting elements.

4. The apparatus of claim 3, further comprising a lens for collimating light from said light emitting elements.

5. The apparatus of claim 3, wherein individual said light-emitting elements have different emission spectra.

6. The apparatus of claim 5, wherein among said different emission spectra from said individual light-emitting elements are peak wavelengths of about 460 nm and about 560 nm.

7. The apparatus of claim 3, wherein said control circuitry can energize individual said light-emitting elements separately.

8. The apparatus of claim 1, wherein said output of said light-emitting element can be varied with respect to intensity.

9. The apparatus of claim 1, wherein said output of said light-emitting element can be varied with respect to temporal pattern.

10. The apparatus of claim 1 wherein said ocular component is visual sensitivity.

11. The apparatus of claim 1 wherein said adjustment by said test subject involves adjusting said light source so that the light emitted therefrom does not appear to flicker.

12. A method for psychophysical determination of an ocular component in an eye of a test subject, said method comprising:
   providing a test subject;
   employing an apparatus to test said test subject, said apparatus comprising;
      a light source comprising at least one electronically controlled, light-emitting element wherein the output of said light-emitting element can be varied electronically by said test subject;
      control circuitry for energizing said light-emitting element;
      an aperture for presenting a test stimulus from said light-emitting element to a test subject; and
      a head positioning device for aligning an eye of a test subject in a position to view said test stimulus;
   determining the response of said test subject to the output of said light-emitting element; and
   relating said response to the extent or condition of an ocular component in said test subject.

13. The method of claim 12 wherein said ocular component is visual sensitivity.

14. The method of claim 12 wherein said adjustment by said test subject involves adjusting said light source so that the light emitted therefrom does not appear to flicker.

15. A method for psychophysical determination of visual sensitivity in an eye of a test subject, said method comprising:

providing a test subject;

employing an apparatus to test said test subject, said apparatus comprising;
- a light source comprising at least one electronically controlled, light-emitting element wherein the output of said light-emitting element can be varied electronically by the subject until the flicker of said light source appears to be eliminated;
- control circuitry for energizing said light-emitting element;
- an aperture for presenting a test stimulus from said light-emitting element to a test subject; and
- a head positioning device for aligning an eye of a test subject in a position to view said test stimulus;

determining the response of said test subject to the output of said light-emitting element, whereby said subject adjusts the light source until said light source appears to have no flicker; and relating said response to the extent or condition of visual sensitivity in said test subject.

16. An apparatus for psychophysical determination of visual sensitivity in an eye of a test subject, said apparatus comprising:

a light source comprising at least one electronically controlled, light-emitting element wherein the output of said light-emitting element can be varied electronically by the subject until the flicker of said light source appears to be eliminated;

control circuitry for energizing said light-emitting element;

an aperture for presenting a test stimulus from said light-emitting element to a test subject; and a head positioning device for aligning an eye of a test subject in a position to view said test stimulus.

* * * * *

UNITED STATES PATENT AND TRADEMARK OFFICE
CERTIFICATE OF CORRECTION

PATENT NO. : 6,315,412 B1  Page 1 of 1
DATED : November 13, 2001
INVENTOR(S) : D. Max Snodderly et al.

It is certified that error appears in the above-identified patent and that said Letters Patent is hereby corrected as shown below:

Title page,
Item [86], "§ 371 Date: Jun. 12, 2000" should read -- § 371 Date: Jun. 2, 2000 --; and
"§ 102 (e) Date: Jun. 12, 2000" should read -- § 102 (e) Date: Jun. 2, 2000 --;

Column 4,
Line 29, "comparsion" should read -- comparison --; and

Column 14,
Line 64, "(Si)" should read -- (S1) --.

Signed and Sealed this

Nineteenth Day of November, 2002

Attest:

Attesting Officer

JAMES E. ROGAN
Director of the United States Patent and Trademark Office